(12) United States Patent
Choi

(10) Patent No.: US 11,298,092 B2
(45) Date of Patent: Apr. 12, 2022

(54) X-RAY IMAGING DEVICE

(71) Applicants: VATECH Co., Ltd., Gyeonggi-do (KR); VATECH EWOO Holdings Co., Ltd., Gyeonggi-do (KR)

(72) Inventor: Sungil Choi, Gyeonggi-do (KR)

(73) Assignees: VATECH Co., Ltd., Gyeonggi-do (KR); VATECH EWOO Holdings Co., Ltd., Gyeonggi-do (KR)

( * ) Notice: Subject to any disclaimer, the term of this patent is extended or adjusted under 35 U.S.C. 154(b) by 574 days.

(21) Appl. No.: 15/500,093

(22) PCT Filed: Jul. 29, 2015

(86) PCT No.: PCT/KR2015/007904
§ 371 (c)(1),
(2) Date: Jan. 29, 2017

(87) PCT Pub. No.: WO2016/018059
PCT Pub. Date: Feb. 4, 2016

(65) Prior Publication Data
US 2017/0245813 A1 Aug. 31, 2017

(30) Foreign Application Priority Data
Jul. 29, 2014 (KR) .................. 10-2014-0096197

(51) Int. Cl.
*A61B 6/14* (2006.01)
*A61B 6/03* (2006.01)
(Continued)

(52) U.S. Cl.
CPC .................. *A61B 6/14* (2013.01); *A61B 6/03* (2013.01); *A61B 6/4435* (2013.01);
(Continued)

(58) Field of Classification Search
CPC .. A61B 6/025; A61B 6/03; A61B 6/14; A61B 6/4435; A61B 6/4452;
(Continued)

(56) References Cited

U.S. PATENT DOCUMENTS

| | | |
|---|---|---|
| 5,692,027 A | 11/1997 | Yoshimura et al. |
| 5,784,429 A | 7/1998 | Arai |
| 5,880,815 A | 3/1999 | Yamamura et al. |
| 2006/0239400 A1 | 10/2006 | Sukovic et al. |

(Continued)

FOREIGN PATENT DOCUMENTS

| | | |
|---|---|---|
| EP | 3195804 A1 | 7/2017 |
| JP | 07-327985 A | 12/1995 |

(Continued)

OTHER PUBLICATIONS

European Patent Office, Extended European Search Report of corresponding EP Patent Application No. 15826603.1, dated Jun. 8, 2018.

*Primary Examiner* — Anastasia Midkiff
(74) *Attorney, Agent, or Firm* — IP Legal Services, LLC

(57) ABSTRACT

Disclosed is an X-ray imaging device, which is capable of providing a tomographic image of an image layer disposed between an axis of rotation and an X-ray source. The imaging device according to the present invention includes a radiography unit having an X-ray source and an X-ray sensor disposed to face each other with a rotating axis therebetween, wherein the X-ray sensor configured to obtain X-ray transmission images, a driver configured to rotate the X-ray source and the X-ray sensor about the rotating axis, and an image processor configured to provide a two-dimensional tomographic image of an image layer disposed between the rotating axis and the X-ray source, by shifting and overlapping the X-ray transmission images after reversing left and right at least some of the X-ray transmission images.

1 Claim, 6 Drawing Sheets

(51) Int. Cl.
  *A61B 6/00* (2006.01)
  *G06T 11/00* (2006.01)
  *G01N 23/046* (2018.01)
  *G06T 3/00* (2006.01)
  *A61B 6/02* (2006.01)

(52) U.S. Cl.
  CPC .......... *A61B 6/4452* (2013.01); *A61B 6/5205* (2013.01); *G01N 23/046* (2013.01); *G06T 11/005* (2013.01); *A61B 6/025* (2013.01); *G06T 3/00* (2013.01); *G06T 2207/10072* (2013.01); *G06T 2207/10116* (2013.01); *G06T 2207/30036* (2013.01)

(58) Field of Classification Search
  CPC ...... A61B 6/5205; G01N 23/046; G06T 3/00; G06T 11/005; G06T 2207/10072; G06T 2207/10116; G06T 2207/30036
  See application file for complete search history.

(56) References Cited

U.S. PATENT DOCUMENTS

| | | |
|---|---|---|
| 2008/0267343 A1 | 10/2008 | Sukovic et al. |
| 2010/0080438 A1 | 4/2010 | Nishimura et al. |
| 2012/0224762 A1 | 9/2012 | Choi et al. |
| 2012/0307960 A1 | 12/2012 | Choi et al. |
| 2014/0193768 A1 | 7/2014 | Ogawa et al. |
| 2015/0305696 A1 | 10/2015 | Yamakawa et al. |
| 2017/0281101 A1 | 10/2017 | Choi et al. |

FOREIGN PATENT DOCUMENTS

| | | |
|---|---|---|
| JP | 09-197582 A | 7/1997 |
| JP | 2002-219127 A | 8/2002 |
| JP | 2009-254472 A | 11/2009 |
| KR | 10-2010-0120815 A | 11/2010 |
| KR | 10-2011-0083153 A | 7/2011 |
| KR | 10-1094180 B1 | 12/2011 |
| KR | 10-2014-0008287 A | 1/2014 |
| WO | 2008/143168 A1 | 11/2008 |

--Related Art--

-- Related Art --

X-RAY IMAGING DEVICE

CROSS REFERENCE TO RELATED APPLICATIONS

This application is a National Stage Patent Application of PCT International Patent Application No. PCT/KR2015/007904 (filed on Jul. 29, 2015) under 35 U.S.C. § 371, which claims priority to Korean Patent Application No. 10-2014-0096197 (filed on Jul. 29, 2014), the teachings of which are incorporated herein in their entireties by reference.

TECHNICAL FIELD

The present invention generally relates to a two-dimensional tomographic imaging device and a method for same. More particularly, the present invention relates to an imaging device and a method for same, in which an X-ray imaging device includes an X-ray source and an X-ray sensor facing each other with an object therebetween, and a driver driving the X-ray source and the X-ray sensor about a rotating axis therebetween, whereby the X-ray imaging device is capable of providing a two-dimensional tomographic image of an image layer disposed between the rotating axis of the driver and the X-ray source.

BACKGROUND ART

X-rays are attenuated according to an X-ray attenuation coefficient, such as photoelectric effect, Compton scattering, and the like, of a substance placed in a path of the X-rays.

X-ray imaging modality is radiography using permeability of X-rays, in which an X-ray image of an inner structure of an object is obtained based on an amount of attenuation that is accumulated in the process of the X-rays passing through the object. To achieve this, an X-ray imaging device includes: an X-ray source emitting X-rays toward an object; an X-ray sensor disposed to face the X-ray source with the object therebetween, and configured to receive the X-rays having passed through the object; and an image processor configured to produce an X-ray image by using a detection result of the X-ray sensor.

X-ray imaging modality provides various X-ray images according to imaging methods and purposes.

As an example, an X-ray panoramic image is obtained through the following process: radiographing by moving the X-ray source and the X-ray sensor along an object, namely, a mandibular arch of an examinee while the X-ray source and the X-ray sensor face each other; and showing a transmission image by joining the radiographs and spreading arrangement relationship of teeth and a tissue therearound of a desired focus layer on a jawbone trajectory. To achieve this, the X-ray source and the X-ray sensor perform rotational movement along a rotating axis therebetween within a predetermined angular range (±135° or less in left and right directions based on a front of the examinee), and perform linear movement in forward and backward directions of the examinee within a predetermined length range.

The X-ray panoramic image is used as a standard image, which is the most familiar to dentists, since the entire arrangement relationship of teeth and tissue therearound can be easily identified.

FIG. 1 shows radiographing teeth arrangement in multiple directions in a conventional dental X-ray panoramic imaging device.

The conventional dental X-ray panoramic imaging device includes a rotating arm with an X-ray source and an X-ray sensor being disposed at opposite sides thereof to face each other, and is configured such that rotating axis C1, C2, C3 is moved along an imaginary centerline connecting a forward direction with a backward direction of teeth arrangement (so called, two-axis drive) along with rotation of the rotating arm, and a transmission path of X-ray beam B1, B2, B3 and X-ray sensor S1, S2, S3 are positioned to be at different locations from each other, whereby a plurality of X-ray transmission images of teeth arrangement of an examinee are radiographed. Further, the radiographed transmission images are shifted in a moving direction of the X-ray sensor S1, S2, S3, and are partially overlapped with each other, whereby an X-ray panoramic image focused on the image layer is produced. In this process, a cross section existing in the image layer appears sharper, while parts existing in other layers appear blurred.

However, the conventional dental X-ray panoramic imaging device has some limitations. One of the limitations is that even when the image layer between the rotating axis and the X-ray sensor is radiographed, a portion between the rotating axis and the X-ray source affects a panoramic image. For example, in the case of imaging anterior teeth in a state where the rotating axis is disposed at a center of the teeth arrangement and the X-ray sensor is disposed in front of the examinee, the cervical vertebrae between the rotating axis and the X-ray source attenuates most of the X-rays, whereby a cervical effect occurs, in which gradation of the anterior teeth appears lighter than the others in a panoramic image.

Another one is that due to a physical limitation of a device configuration, an image layer, which is allowed to be radiographed as an X-ray panoramic image, is limited to layers between the X-ray sensor and the rotating axis of the rotating arm. Thereby, it is impossible to perform a postero-anterior view (PA) mode imaging of a temporo mandibular joint (TMJ), which is mainly used for diagnosis in dental care, that is, impossible to radiograph an image layer of the TMJ shown as a cross section perpendicular to an extension direction of a jawbone.

FIG. 2 shows a problem occurring when attempting TMJ PA mode imaging by using conventional dental X-ray panoramic imaging device.

The following cases use a general dental X-ray panoramic imaging device as a model, in which a distance FDD from the X-ray source to the X-ray sensor is between 450 mm and 600 mm, and a magnification rate is between 1.2 and 1.5.

Case A) In the case of imaging PA mode image layer TR when a rotating axis Ca of the rotating arm is disposed at the center of an examinee's teeth arrangement, and an X-ray beam Ba is irradiated from a left front of an examinee toward a right TMJ, the X-ray sensor intrudes into the right of a head of the examinee, thus in reality it is impossible to radiograph the area.

Case B) In the case of imaging PA mode image layer TL when a rotating axis Cb of the rotating arm is disposed at a center of a left TMJ and a right TMJ, and an X-ray beam Bb is irradiated from a right of the examinee toward a left TMJ, an irradiation angle of the X-ray beam Bb is almost in parallel to the image layer TL, whereby it is difficult to obtain a TMJ PA mode image.

Case C) In the case of imaging PA mode image layer TL when a rotating axis Cc of the rotating arm is disposed near the cervical vertebrae of the examinee, and an X-ray beam Bc is irradiated from a right rear of the examinee toward the left TMJ, the X-ray sensor also intrudes into the right of the head of the examinee, thus it is impossible to radiograph the area.

For the above reasons, TMJ PA mode imaging is not realized in the conventional X-ray panoramic imaging device having a two-axis drive system, but is provided only in a device having a three-axis drive system, that is, a mechanically larger, more complex and more expensive device capable of moving a location of the rotating axis two-dimensionally.

DISCLOSURE

Technical Problem

Accordingly, the present invention has been made keeping in mind the above problems occurring in the related art, and the present invention is intended to propose a two-dimensional tomographic imaging device and a method for same that can provide a tomographic image of an image layer disposed between a rotating axis and an X-ray source. The present invention is further intended to propose a two-dimensional tomographic imaging device and a method for same that can perform a TMJ PA mode imaging, which is conventionally possible in a three-axis drive system, with a mechanical configuration that is similar to a dental X-ray panoramic imaging device using a conventional two-axis drive system.

Technical Solution

In order to achieve the above object, according to some aspect of the present invention, there is provided a two-dimensional tomographic imaging device including: a radiography unit having an X-ray source and an X-ray sensor disposed to face each other with a rotating axis therebetween; a driver configured to rotate the X-ray source and the X-ray sensor about the rotating axis; and an image processor configured to provide a two-dimensional tomographic image of an image layer disposed between the rotating axis and the X-ray source, by using X-ray transmission images obtained during unit drive of the driver.

The image processor may be configured such that at least some of the X-ray transmission images are reversed left to right, and the reversed X-ray transmission images are shifted in a moving direction of the X-ray sensor and overlapped with each other, whereby the two-dimensional tomographic image of the image layer is provided.

In order to achieve the above object, according to some aspect of the present invention, there is provided a two-dimensional tomographic imaging device including: radiography unit having an X-ray source and an X-ray sensor disposed to face each other with a rotating arm and a rotating axis of the rotating arm therebetween; a driver configured to drive the radiography unit so as to include a first axis drive rotating the rotating arm, and a second axis drive moving the rotating axis of the rotating arm along a linear trajectory; and an image processor configured to provide a two-dimensional tomographic image of an image layer disposed between the rotating axis and the X-ray source, by using X-ray transmission images obtained during unit drive of the driver.

The image processor may be configured such that at least some of the X-ray transmission images are reversed left to right, and the reversed X-ray transmission images are shifted in a moving direction of the X-ray sensor in response to a rotation direction of the rotating arm and overlapped with each other, whereby the two-dimensional tomographic image of the image layer is provided.

The image layer may include an image layer of a temporo mandibular joint (TMJ) in a postero-anterior view (PA) mode, in which a temporo mandibular joint (TMJ) of an examinee is shown as a cross section perpendicular to an extension direction of a jawbone.

A distance from the X-ray source to the X-ray sensor may be 1000 mm or less.

A distance from the X-ray source to the X-ray sensor may be 300 mm or more and may be 700 mm or less.

In order to achieve the above object, according to some aspect of the present invention, there is provided a two-dimensional tomographic imaging method including: an imaging step of rotating an X-ray source and an X-ray sensor disposed to face each other with a rotating axis therebetween about the rotating axis, and imaging a plurality of X-ray transmission images; and an image production step of reversing at least some of the X-ray transmission images left to right, and shifting the reversed X-ray transmission images in a moving direction of the X-ray sensor and overlapping each other, thereby producing a two-dimensional tomographic image of a rear image layer disposed between the rotating axis and the X-ray source.

The image production step may produce a two-dimensional tomographic image of a front image layer disposed between the rotating axis and the X-ray sensor.

In order to achieve the above object, according to some aspect of the present invention, there is provided a two-dimensional tomographic imaging device including: an X-ray source and an X-ray sensor facing each other with an object therebetween; a driver configured to perform radiography by rotating the X-ray source and the X-ray sensor about a rotating axis disposed therebetween; and an image processor configured to provide a first tomographic image of a front image layer within the object between the rotating axis and the X-ray sensor, and to provide a second tomographic image of a rear image layer within the object between the rotating axis and the X-ray source, by using results of unit cycle radiography of the driver.

In order to achieve the above object, according to some aspect of the present invention, there is provided a two-dimensional tomographic imaging device including: an X-ray source and an X-ray sensor facing each other with a mandibular arch therebetween; a driver configured to perform radiography by rotating the X-ray source and the X-ray sensor about a rotating axis disposed therebetween; and an image processor configured to provide a panoramic image of a trajectory of the mandibular arch, and to provide a postero-anterior view (PA) tomographic image of a temporo mandibular joint (TMJ), by using results of unit cycle radiography of the driver.

In anyone of the two-dimensional tomographic imaging devices described right above, the driver may be configured to rotate and rectilinearly move the rotating axis during at least a portion of the unit cycle.

The image processor may be configured such that at least some of the radiography results are reversed left to right, and the reversed radiography results are shifted in a moving direction of the X-ray sensor according to a rotation direction of the rotating axis and overlapped with each other, whereby the second tomographic image of the rear image layer is produced.

In order to achieve the above object, according to some aspect of the present invention, there is provided an X-ray panoramic two-dimensional tomographic imaging device configured to provide a panoramic image and a temporo mandibular joint (TMJ) postero-anterior view (PA) mode image of a trajectory of a mandibular arch by using a single scan driving system.

In order to achieve the above object, according to some aspect of the present invention, there is provided a two-dimensional tomographic imaging device including: an X-ray sensor configured to move along a trajectory of a mandibular arch of an examinee in front of the mandibular arch; an X-ray source configured to move to face the X-ray sensor based on a rotating axis between the trajectory of the mandibular arch and a temporo mandibular joint (TMJ); and an image processor configured to provide a tomographic image of an image layer between the rotating axis and the X-ray source, by using a detection result of the X-ray sensor. Herein, the two-dimensional tomographic image may be a postero-anterior view (PA) tomographic image of the TMJ.

Advantageous Effects

According to the present invention having the above-described characteristics, it is possible to provide a tomographic image of an image layer disposed between a rotating axis and an X-ray source, thereby enabling a TMJ PA mode imaging, which is conventionally possible in a three-axis drive system, with a mechanical configuration that is similar to a dental X-ray panoramic imaging device using a conventional two-axis drive system, and thus the present invention is advantageous for miniaturization and is easy to operate.

MODE FOR INVENTION

Reference will now be made in greater detail to exemplary embodiments of the present invention, an example of which is illustrated in the accompanying drawings. Although preferred embodiments of the present invention have been described for a dental X-ray panoramic imaging device, those skilled in the art will appreciate that the present invention can be applied to a two-dimensional tomographic imaging device, without departing from the scope and spirit of the invention as disclosed in the accompanying claims.

Figure 3:
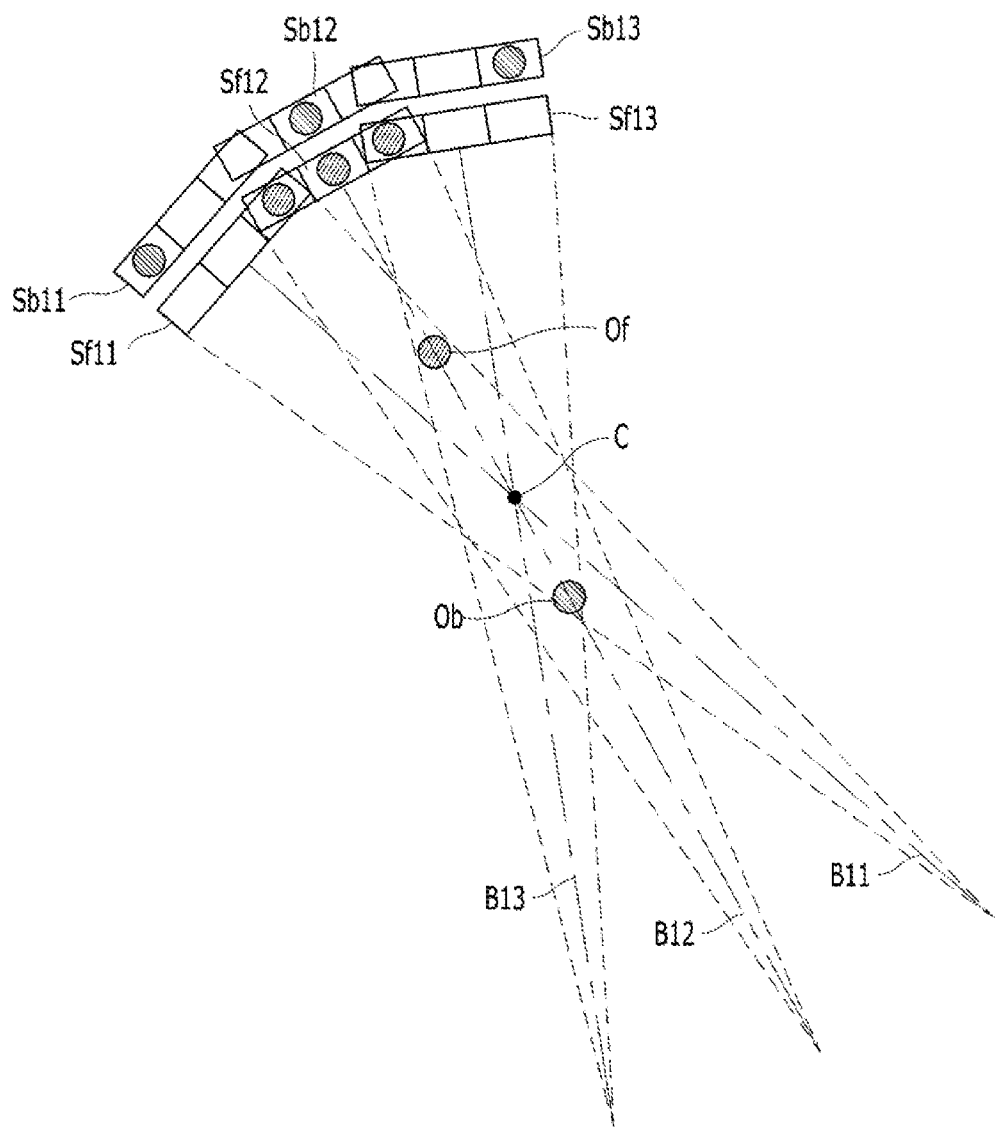
FIG. 3 shows radiographing in multiple directions in a two-dimensional tomographic imaging device according to an embodiment of the present invention.

FIG. 3 shows radiographing in multiple directions in a two-dimensional tomographic imaging device according to an embodiment of the present invention.

Figure 1:
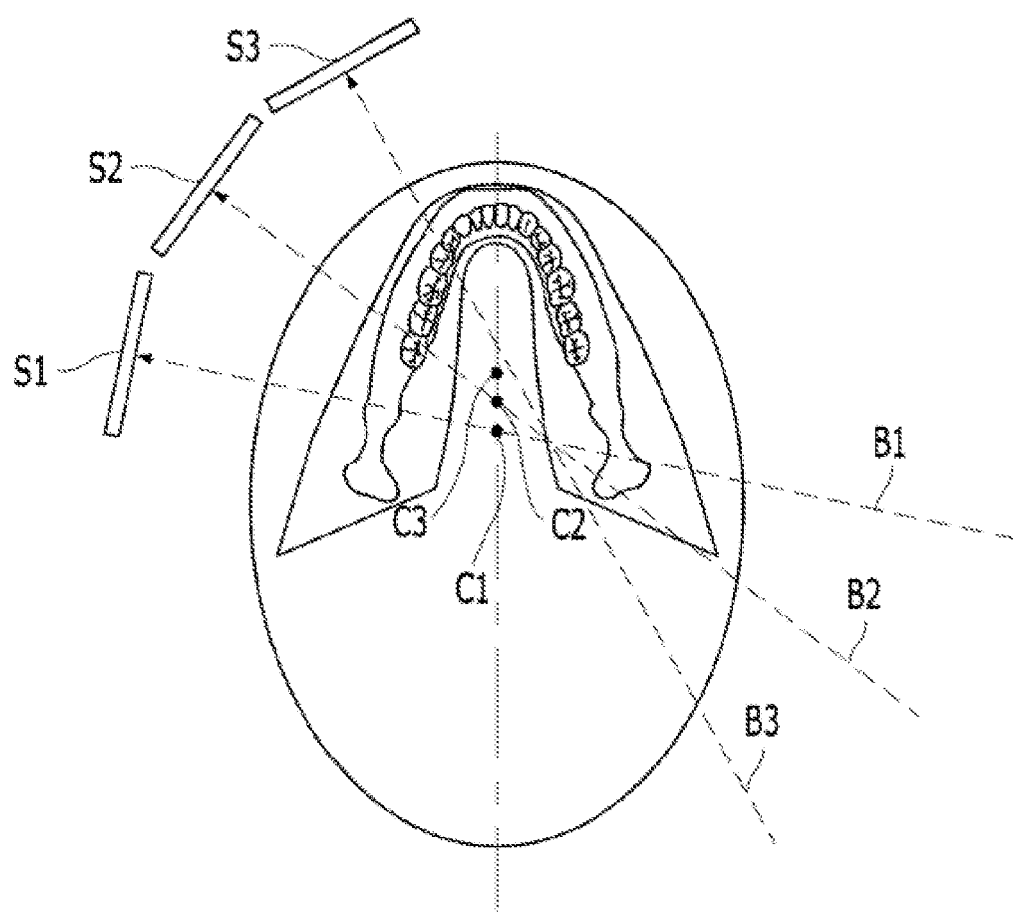
FIG. 1 shows radiographing teeth arrangement in multiple directions in a conventional dental X-ray panoramic imaging device.

The two-dimensional tomographic imaging device according to the embodiment of the present invention includes: a radiography unit having an X-ray source and an X-ray sensor disposed to face each other with a rotating axis therebetween; and a driver configured to rotate the X-ray source and the X-ray sensor about the rotating axis. Here, in the radiography unit, a distance between the X-ray source and the X-ray sensor may be 1000 mm or less, and preferably, is 300 mm or more and is 700 mm or less. As described in the conventional dental X-ray panoramic imaging device with reference to FIG. 1, this configuration may be easily understood by those skilled in the art, so a detailed description of a mechanical configuration will be omitted.

Figure 2:
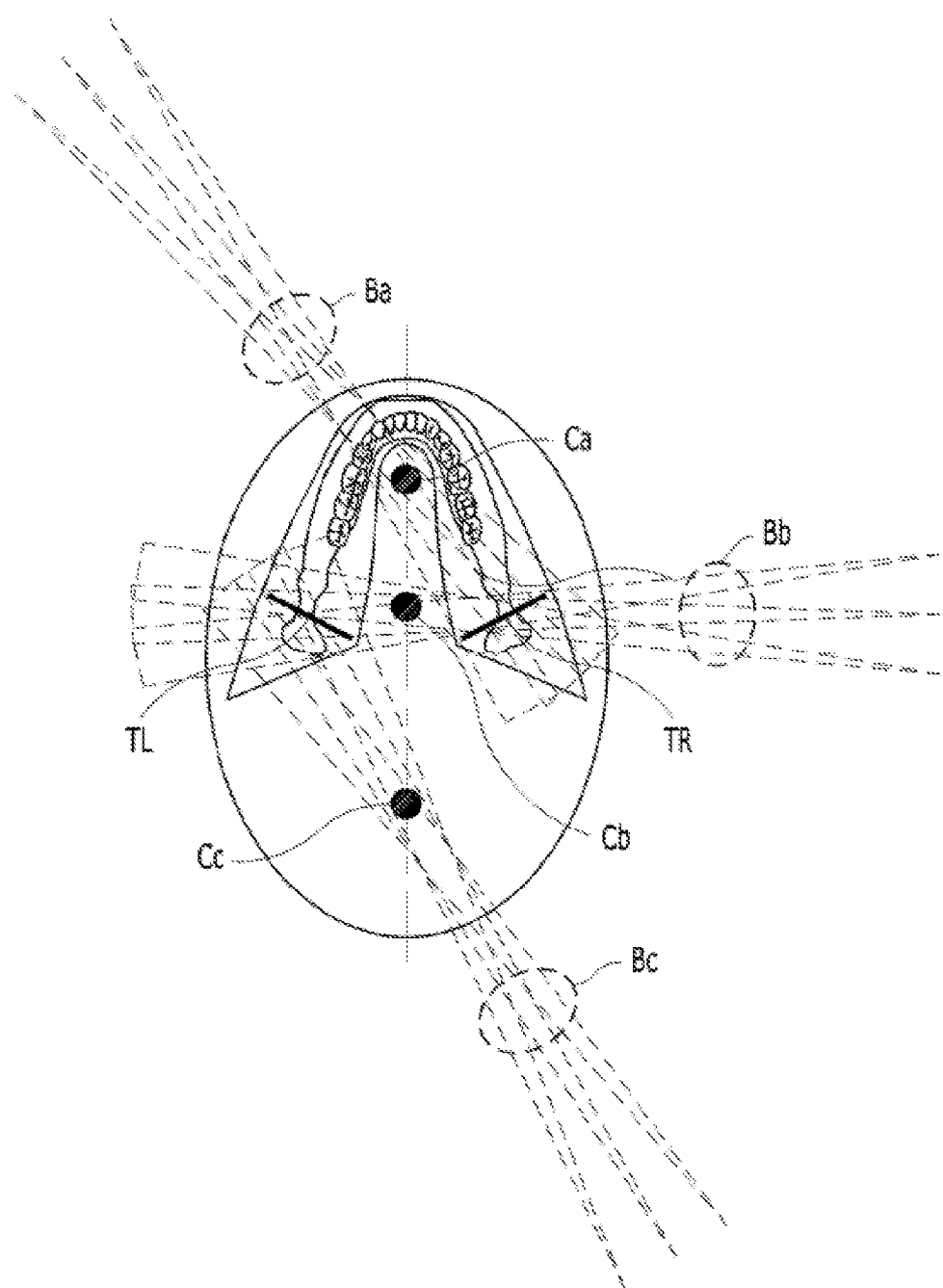
FIG. 2 shows a problem occurring when attempting TMJ PA mode imaging by using conventional dental X-ray panoramic imaging device.

In the process of obtaining a series of images, the radiography unit is rotated about the rotating axis C, and irradiates an X-ray beam B11, B12, B13 from the X-ray source disposed at a side of the radiography unit to the X-ray sensor disposed to face the X-ray source with the rotating axis C therebetween. The X-ray beam B11, B12, B13 passes through a back object Ob and a front object Of on each path thereof, and is incident on the X-ray sensor, thereby providing a transmission image of each path. Herein, the back object Ob refers to an object disposed between the rotating axis C and the X-ray source; and the front object Of refers to an object disposed between the rotating axis C and the X-ray sensor. In reality, the front object Of and the back object Ob are projected to one transmission image, but in the drawings, for convenience of understanding, transmission images Sf11 to Sf13 of the front object Of and transmission images Sb11 to Sb13 of the back object Ob in multiple directions are shown separately. Meanwhile, when a range of a field of view including the front object Of and the back object Ob is narrow, a location of the rotating axis C may be fixed, but as in the case of a dental X-ray panoramic imaging device described with reference to FIGS. 1 and 2, when an image layer, as an object to be radiographed, is over a large area, the rotating axis C may rectilinearly move within a predetermined range, for example, along an imaginary centerline connecting a forward direction with a backward direction of teeth arrangement.

In the process of obtaining a series of images, when an X-ray beam B11 is irradiated in a first direction, an image of the front object Of is formed on the right of a front transmission image Sf11. When an X-ray beam B12 is irradiated in a second direction, the image of the front object Of is formed at a center of a front transmission image Sf12, and when an X-ray beam B13 is irradiated in a third direction, the image of the front object Of is formed on the left of a front transmission image Sf13. Meanwhile, an image of the back object Ob is formed on the left of a back transmission image Sb11 to the X-ray beam B11 in the first direction, at a center of a back transmission image Sb12 to the X-ray beam B12 in the second direction, and on the left of a back transmission image Sb13 to the X-ray beam B13 in the third direction.

The two-dimensional tomographic imaging device according to the embodiment is configured such that a two-dimensional tomographic image respectively focused on desired image layers, that is, an image layer including the front object Of and on an image layer including the back object Ob, is produced and provided by using transmission images formed in multiple directions through an image processor. A configuration of the image processor and an imaging method will be described, hereinbelow.

Figure 4A:
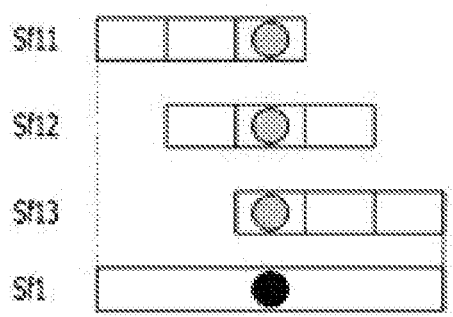
FIGS. 4A and 4B schematically show producing a tomographic image of a front image layer in a two-dimensional tomographic imaging device according to an embodiment of the present invention.
Figure 4B:
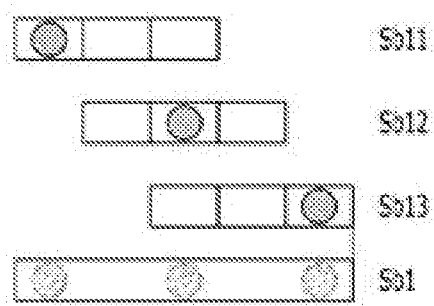

FIGS. 4A and 4B schematically show producing a tomographic image of a front image layer in a two-dimensional tomographic imaging device according to an embodiment of the present invention.

FIG. 4A shows producing a two-dimensional tomographic image Sf1 of the front object Of by shifting transmission images formed an image of the front object Of thereon in a moving direction of the X-ray sensor according to an imaging direction, that is, by moving the transmission images in parallel, and by overlapping the transmission images with each other, in the image processor. When a plurality of front transmission images Sf11 to Sf13 is overlapped while being moved in parallel as described above, images of the front object Of are overlapped with each other, thereby forming a focused sharp image.

Meanwhile, FIG. 4B shows that the image of the back object Ob is blurred to fade away from a two-dimensional tomographic image Sb1 consequentially produced when the same method as FIG. 4A is applied to an image of the back object Ob. Herein, for convenience of understanding, the two-dimensional tomographic image f1 of the front object Of and the two-dimensional tomographic image Sb1 of the back object Ob are shown separately, but in reality, these are provided as one two-dimensional tomographic image, so through the above imaging method, only a two-dimensional tomographic image of an image layer including the front object Of can be obtained.

Figure 5:
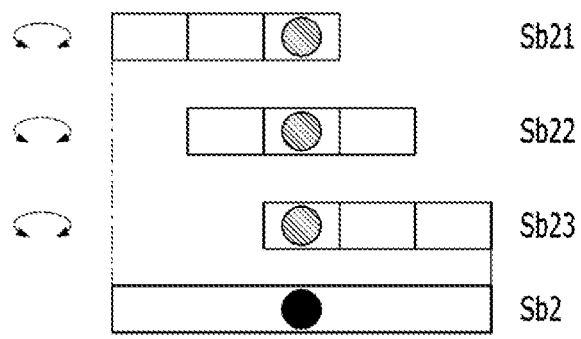
FIG. 5 schematically shows producing a tomographic image of a rear image layer in a two-dimensional tomographic imaging device according to an embodiment of the present invention.

FIG. 5 schematically shows producing a tomographic image of a rear image layer in a two-dimensional tomographic imaging device according to an embodiment of the present invention. The image processor of the two-dimensional tomographic imaging device according to the embodiment performs the following imaging method to provide a two-dimensional tomographic image focused on an image layer including the above mentioned back object Ob.

Firstly, as shown in FIG. 4B, back transmission images Sb11, Sb12, and Sb13, where an image of the back object Ob is projected (herein, for convenience of understanding, the image of the back object shown, but in reality, both the front object and the back object projected) are respectively reversed left to right. The reversed back transmission images Sb11, Sb12, and Sb13 are overlapped with each other while being moved in parallel in a moving direction of the X-ray sensor according to an imaging direction. As a result, it is possible to provide a two-dimensional tomographic image Sb2 focused on an image layer including the back object Ob. In reality, the images of the back object Ob are overlapped at the same location to be focused sharply, and the images of the front object Of are distributed to be blurred on a plurality of transmission images.

Figure 6:
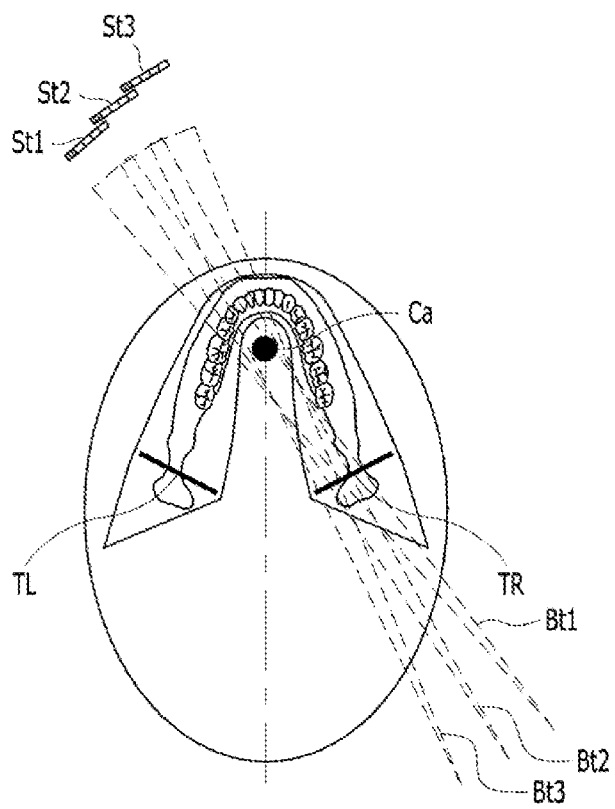
FIG. 6 shows radiographing a tomographic image of an image layer of a in an X-ray panoramic imaging device according to an embodiment of the present invention.

FIG. 6 shows radiographing a tomographic image of an image layer of a in an X-ray panoramic imaging device according to an embodiment of the present invention.

As shown in the drawing, a temporo mandibular joint of the examinee, namely, a TMJ is disposed between a rotating axis Ca and an X-ray source in the X-ray panoramic imaging device, wherein when the imaging method described with reference to FIG. 5 and the X-ray panoramic imaging device having the image processor performing the method are used, it is possible to obtain a two-dimensional tomographic image of an image layer including a TMJ. In particular, it is possible to obtain an image of an image layer corresponding to a TMJ PA mode, which is mainly used for diagnosis in dental care.

Herein, the rotating axis Ca is shown as one point, but may be moved along a centerline of the teeth arrangement. Along with movement of the rotating axis Ca, the X-ray source and the X-ray sensor are rotated about the rotating axis Ca, and X-ray beams Bt1 to Bt3 are irradiated in multiple directions, whereby a plurality of transmission images St1 to St3, in which the X-ray beams have passed through the TMJ in a direction near an extension line of the TMJ of the teeth arrangement, is obtained. The obtained transmission images St1 to St3 are respectively reversed left to right in the image processor as described with reference to FIG. 5, and then the images are overlapped with each other while being moved in parallel in a moving direction (in the drawing, clockwise) of the X-ray sensor according to an imaging direction. In other words, in a plurality of transmission images St1 to St3 shown in the drawing, hatched parts are disposed on the left, but the images are reversed such that these parts are disposed on the right, and are overlapped with each other while being sequentially shifted clockwise (moved in parallel), whereby a two-dimensional tomographic image of an image layer corresponding to the TMJ PA mode is produced.

Figure 7:
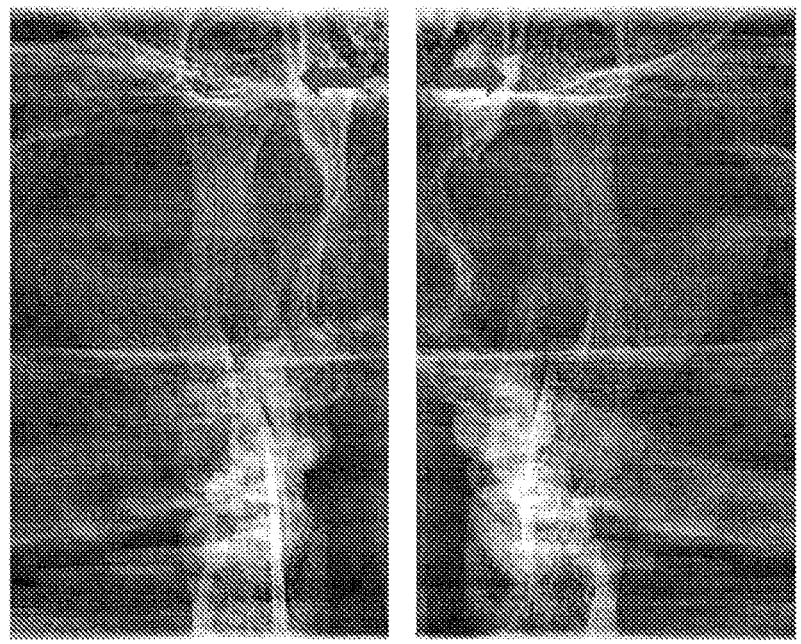
FIG. 7 shows a TMJ PA mode tomographic image radiographed according to the embodiment of FIG. 6.

FIG. 7 shows a TMJ PA mode tomographic image radiographed according to the embodiment of FIG. 6. In the picture, it can be identified that a part indicated by an arrow corresponds to a cross section of the PA mode of the TMJ.

Meanwhile, the two-dimensional tomographic imaging device and the X-ray panoramic imaging device according to the embodiments of the present invention are capable of providing two-dimensional tomographic images of image layers at various locations between the X-ray source and the X-ray sensor, as well as an image layer including teeth arrangement or TMJ, wherein as an imaging method for various image layers, an art disclosed in the document of Korean Patent No. 10-1094180 titled "Method and apparatus for obtaining panoramic image", which is invented by the same inventor as the present invention, can be used.

The invention claimed is:

1. An X-ray imaging device comprising:
a radiography unit having an X-ray source and an X-ray sensor, wherein the X-ray source and the X-ray sensor are disposed to face each other with a rotating axis therebetween and rotate about the rotating axis in a first direction, the X-ray sensor is configured to obtain a plurality of X-ray transmission images; and
an image processor configured to generate a two-dimensional tomographic image of a target object in a region of interest in a patient's predetermined region, another object in a different image layer of the same region partially blocking said target object from being directly detected by the X-ray sensor, said image processor further configured to: flip the image orientation, in a left to right direction, of at least some of said plurality of X-ray transmission images of the target realign all of the flipped X-ray transmission images with each other in the first direction, such that the image of the target object in the flipped X-ray transmission images appears at a same position within each flipped transmission image, and overlaying the realigned, flipped X-ray transmission images on each other, such that the images of the target object overlap within each of the flipped, aligned, and overlaid transmission images to create said two-dimensional tomographic image.

* * * * *